United States Patent [19]
Targan et al.

[11] Patent Number: 5,937,862
[45] Date of Patent: Aug. 17, 1999

[54] METHODS OF DETERMINING THE RISK OF POUCHITIS DEVELOPMENT

[75] Inventors: Stephan R. Targan, Santa Monica; Phillip Fleshner, Beverly Hills, both of Calif.; Scott E. Plevy, Tenafly, N.J.

[73] Assignee: Cedars-Sinai Medical Center, Los Angeles, Calif.

[21] Appl. No.: 08/833,388

[22] Filed: Apr. 4, 1997

Related U.S. Application Data

[63] Continuation of application No. 08/631,429, Apr. 12, 1996, abandoned.
[51] Int. Cl.$^6$ .................................................. A61B 19/00
[52] U.S. Cl. ............................................. 128/898; 435/4
[58] Field of Search ............................... 128/898; 435/4, 435/7.24; 604/64; 600/300, 309, 310, 317

[56] References Cited

PUBLICATIONS

Fleshner et al., A Rise in pANCA Titre after Ileal Pouch Anal Anostomosis for Ulcerative Colitis May Predict Early Pouchitis. *Gastroenterology.* 110:A907 (1996).
Hanauer, "Inflammatory Bowel Disease," *New Eng. J. Med.* 334:841–848 (1996).
Madden et al., "Inflammation in Ileal Reservoirs: 'Pouchitis,'" *Gut* 31:247–249 (1990).
Patel et al., "Influence of total colectomy on serum antineutrophil cytoplasmic antibodies in inflammatory bowel disease," *British Journal of Surgery* 81:724–726 (1994).
Pemberton, "The Problem with Pouchitis," *Gastroenterol.* 104:1209–1211 (1993).
Reumaux et al., "Antineutrophil Cytoplasmic Auto–Antibodies in Sera From Patients After Proctocolectomy for Ulcerative Colitis,"*Gastroenterol.* 104:A769 (1993).
Sandborn, "Antineutrophil Cytoplasmic Antibody Correlates with Chronic Pouchitis after Ileal Pouch–Anal Anastomosis," *Amer. J. Gastroenterol.* 90:740–747 (1995).
Sandborn et al., "Pouchitis After Ileal Pouch–Anal Anastomosis: A Pouchitis Disease Activity Index," *Mayo Clin. Proc.* 69:409–415 (1994).
Sandborn, "Pouchitis Following Ileal Pouch–Anal Anastomosis: Definition, Pathogenesis, and Treatment," *Gastroenterol.* 107:1856–1860 (1994).
Sandborn et al., "The Presence of Antineutrophil Cytoplasmic Antibody Correlates with Pouchitis After Ileal Pouch–anal Anastomosis for Ulcerative Colitis," *Gastroenterol.* 104: A774 (1993).
Saxon et al., "A Distinct Subset of Antineutrophil Cytoplasmic Antibodies is Associated with Inflammatory Bowel Disease," *J. Allergy Clin. Immunol.* 86:202–210 (1990).
Shepherd et al., "Workshop: Pouchitis," *Int. J. Colorectol. Dis.* 4:205–229 (1989).
Tytgat and van Deventer, "Pouchitis," *Int. J. Colorect. Dis.* 3:226–228 (1988).
Vecchi et al., "P–ANCA and Development of Pouchitis in Ulcerative Colitis Patients After Proctocolectomy and Ileoanal Pouch Anastomosis," *The Lancet* 344:886–887 (1994).

*Primary Examiner*—Mickey Yu
*Assistant Examiner*—Kelly O'Hara
*Attorney, Agent, or Firm*—Campbell & Flores

[57] ABSTRACT

Provided is a method of determining a risk of pouchitis development following a surgical procedure whereby colon is removed and an internal pouch is created in a patient with UC by determining a first pANCA titer, where the first pANCA titer is determined following the surgical procedure; determining a second pANCA titer at a later time; and comparing the first pANCA titer and the second pANCA titer, where a significantly elevated second pANCA titer indicates an increased risk of pouchitis development. Also provided is a method of determining a risk of pouchitis development following a surgical procedure whereby colon is removed and an internal pouch is created in a patient with UC by determining a first pANCA titer, where the first pANCA titer is determined prior to the surgical procedure; determining a second pANCA titer following said surgical procedure; and comparing the first pANCA titer and the second pANCA titer, where a significantly elevated second pANCA titer indicates an increased risk of pouchitis development.

26 Claims, No Drawings

METHODS OF DETERMINING THE RISK OF POUCHITIS DEVELOPMENT

RELATED APPLICATIONS

This application claims the benefit of U.S. Provisional application Ser. No. 60/631,429, filed Apr. 12, 1996, now abandoned, which was converted from application Ser. No. 08/631,429 and which is incorporated herein by reference.

ACKNOWLEDGMENT

This work was supported by USPHS grant DK46763 awarded by The United States Public Health Service. The United States government has certain rights in this invention.

BACKGROUND OF THE INVENTION

1. Field of the Invention

The invention relates generally to the fields of autoimmunity and inflammatory bowel disease and more specifically to the development of pouchitis in patients with ulcerative colitis.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe and in ulcerative colitis often is accompanied by bleeding. Anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Progress has been made in diagnosing IBD and in distinguishing, in many cases, Crohn's disease from ulcerative colitis. However, CD and UC each can represent a collection of heterogeneous disease types that affect the gastrointestinal tract and produce similar symptoms. One aspect of the heterogeneity associated with inflammatory bowel disease is revealed by the stark contrast in outcomes seen following colectomy for treatment of uncontrolled ulcerative colitis. The preferred procedure is abdominal colectomy with ileal pouch anal anastomosis (IPAA), whereby the diseased colonic mucosa is removed while continence is maintained through creation of an ileal reservoir or "pouch." Although a subgroup of UC patients experience a favorable outcome following surgery, over time as many as 47% develop "pouchitis," which is an inflammation of the pouch that can mimic the original symptoms of UC. A method of determining the subgroup of UC patients at increased risk for development of pouchitis would be useful in the medical management of these patients following surgery. Unfortunately, a method of predicting the development of pouchitis currently is not available. Thus, there is a need to determine the risk of developing pouchitis following pouch surgery. The present invention satisfies this need and provides related advantages as well.

SUMMARY OF THE INVENTION

The present invention provides a method of determining the risk of pouchitis development following a surgical procedure whereby colon is removed and an internal pouch is created in a patient with UC by determining a first pANCA titer, where the first pANCA titer is determined following the surgical procedure; determining a second pANCA titer at a later time; and comparing the first pANCA titer and the second pANCA titer, where a significantly elevated second pANCA titer indicates an increased risk of pouchitis development. The method also can include determining one or more subsequent pANCA titers at one or more subsequent times and comparing a subsequent pANCA titer with an earlier pANCA titer, where a significantly elevated subsequent pANCA titer indicates an increased risk of pouchitis development.

The invention further provides a method of determining a risk of pouchitis development following a surgical procedure whereby colon is removed and an internal pouch is created in a patient with UC by determining a first pANCA titer, where the first pANCA titer is determined prior to the surgical procedure; determining a second pANCA titer following said surgical procedure; and comparing the first pANCA titer and the second pANCA titer, where a significantly elevated second pANCA titer indicates an increased risk of pouchitis development. The method also can include determining one or more subsequent pANCA titers at one or more subsequent times and comparing a subsequent pANCA titer with an earlier pANCA titer, where a significantly elevated subsequent pANCA titer indicates an increased risk of pouchitis development. The methods of the invention are useful, for example, in determining the risk of early-onset pouchitis, acute pouchitis or chronic pouchitis following a surgical procedure such as colectomy with ileal pouch anal anastomosis.

DETAILED DESCRIPTION OF THE INVENTION

The present invention is directed to the discovery of methods for determining the risk of developing pouchitis, which is an unfortunate complication of surgery for uncontrolled ulcerative colitis (UC). The convenient, non-invasive methods of the invention are based on determining titers of perinuclear anti-neutrophil cytoplasmic antibodies. Such methods allow earlier treatment of patients at increased risk for developing pouchitis, while sparing low-risk patients from unnecessary treatment.

Ulcerative colitis is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, *Pathology* (Second Edition) Philadelphia: J. B. Lippincott Company (1994), which is incorporated herein by reference).

As used herein, the term "ulcerative colitis" is synonymous with "UC" and means a disease having clinical features of left-sided colonic disease accompanied by a characteristic endoscopic or histopathologic feature of UC. Clinical features of left-sided colonic disease, as used herein, are rectal bleeding, urgency and tenesmus. The rectal bleeding may be accompanied by mucus discharge. Additional clinical features that may be present in UC include treatment with topical therapy and recommended or performed total or near-total colectomy.

A characteristic endoscopic feature of UC, which when present with clinical features of left-sided colonic disease indicates ulcerative colitis, is inflammation that is more severe distally than proximally or continuous inflammation. Additional typical endoscopic features that may be present in UC include inflammation extending proximally from the rectum or the presence of shallow ulcerations or the lack of deep ulcerations.

A characteristic histopathologic feature of UC, which when present with clinical features of left-sided colonic disease indicates ulcerative colitis, is homogeneous, continuous, predominantly superficial inflammation or a lack of "focality" within biopsy specimens. Additional typical histopathologic features that may be present in UC include the presence of crypt abscesses or a lack of granulomas.

As used herein, the term "patient with UC" means a patient having ulcerative colitis, as defined by the presence of clinical features of left-sided colonic disease accompanied by a characteristic endoscopic or histopathologic feature of UC as defined herein.

In the event that ulcerative colitis is unresponsive to medical therapy, surgical removal of the colon is an option that can remedy the painful symptoms of UC. An unfortunate complication of pouch surgery can be the development of pouchitis, which is non-specific inflammation of a surgically created reservoir, manifest clinically by diarrhea accompanied by additional variable symptoms including abdominal cramping, fecal urgency and bleeding or fever. Pouchitis can be diagnosed clinically by an increase of at least three stools per day above the post-operative base-line (Sandborn et al., *Am. J. Gastroenterol,* 90:740–747 (1995), which is incorporated herein by reference). Characteristic endoscopic features of pouchitis are granularity, friability, loss of vascular pattern, mucous exudate or ulceration of the pouch. As used herein, the term "pouchitis" means a condition manifest clinically by diarrhea combined with one or more of the characteristic endoscopic features of pouchitis.

Pouchitis can develop months or years following pouch surgery. The cumulative frequency of pouchitis increases with time such that 15%, 36% or 46% of patients develop pouchitis 1, 5 or 10 years, respectively, after pouch surgery (Penna et al., *Gastroenterol,* 106:A751 (1994)). The term "early-onset pouchitis," as used herein, means the form of pouchitis that develops within twelve months of a surgical procedure whereby colon is removed and an internal pouch is created.

Pouchitis can occur acutely or as a chronic condition. Acute pouchitis occurs as a single event or as intermittent relapses with pouchitis-free intervals during which suppressive therapy is not required. In contrast, chronic pouchitis, which accounts for about five percent of cases following IPAA, is characterized by persistent symptoms of pouchitis despite adequate medical therapy, or by the need for continuous medical suppressive therapy with a prompt recurrence of symptoms if medical therapy is discontinued. Chronic pouchitis can be treatment-responsive, requiring ongoing suppressive therapy, or can be treatment-resistant. As used herein, the term "pouchitis" encompasses early-onset, acute and chronic pouchitis and includes treatment-responsive and treatment-resistant forms of chronic pouchitis.

As used herein, a "surgical procedure whereby colon is removed and an internal pouch is created" is synonymous with "pouch surgery" and means a surgical procedure that results in total or near-total colectomy and creation of an internal reservoir for maintenance of continence. An internal reservoir can be, for example, an ileal reservoir or ileoanal reservoir. Thus, a surgical procedure whereby colon is removed and an internal pouch is created is, for example, colectomy with ileal pouch anal anastomosis.

The present invention provides a method of determining a risk of pouchitis development following a surgical procedure whereby colon is removed and an internal pouch is created in a patient with UC by determining a first pANCA titer, where the first pANCA titer is determined following the surgical procedure; determining a second pANCA titer at a later time; and comparing the first pANCA titer and the second pANCA titer, where a significantly elevated second pANCA titer indicates an increased risk of pouchitis development. The invention further provides a method of determining a risk of pouchitis development following a surgical procedure whereby colon is removed and an internal pouch is created in a patient with UC by determining a first pANCA titer, where the pANCA titer is determined following the surgical procedure; determining a second pANCA titer at a later time; comparing the first pANCA titer and the second pANCA titer; determining one or more subsequent pANCA titers at one or more subsequent times; and comparing a subsequent pANCA titer with an earlier pANCA titer, where a significantly elevated pANCA titer indicates an increased risk of pouchitis development.

In addition, the invention provides a method of determining a risk of pouchitis development following a surgical procedure whereby colon is removed and an internal pouch is created in a patient with UC by determining a first pANCA titer, where the first pANCA titer is determined prior to the surgical procedure; determining a second pANCA titer following said surgical procedure; and comparing the first pANCA titer and the second pANCA titer, where a significantly elevated second pANCA titer indicates an increased risk of pouchitis development. The invention further provides a method of determining a risk of pouchitis development following a surgical procedure whereby colon is removed and an internal pouch is created in a patient with UC by determining a first pANCA titer, where the pANCA titer is determined prior to the surgical procedure; determining a second pANCA titer at a later time; comparing the first pANCA titer and the second pANCA titer; determining one or more subsequent pANCA titers at one or more subsequent times; and comparing a subsequent pANCA titer with an earlier pANCA titer, where a significantly elevated pANCA titer indicates an increased risk of pouchitis development.

The invention further provides a method of determining a risk of pouchitis development following a surgical procedure whereby colon is removed and an internal pouch is created in a patient with UC by determining a first pANCA titer, where the first pANCA titer is determined following the surgical procedure; determining a second pANCA titer at a later time; and comparing the first pANCA titer and the second pANCA titer, where a comparable or reduced second pANCA titer indicates a decreased risk of pouchitis development. The invention also provides a method of determining a risk of pouchitis development following a surgical procedure whereby colon is removed and an internal pouch is created in a patient with UC by determining a first pANCA titer, where the pANCA titer is determined following the surgical procedure; determining a second pANCA titer at a later time; comparing the first pANCA titer and the second pANCA titer; determining one or more subsequent pANCA titers at one or more subsequent times; and comparing a subsequent pANCA titer with an earlier pANCA titer, where a comparable or reduced pANCA titer indicates a decreased risk of pouchitis development.

The methods of the invention are based on determining titers of anti-neutrophil cytoplasmic antibodies that produce a perinuclear staining pattern (pANCA), which are elevated in 68–80% of UC patients and less frequently in CD and other disorders of the colon. Serum titers of ANCA are elevated regardless of clinical status and, thus, do not reflect disease activity. High levels of serum ANCA also persist in patients five years post-colectomy. Although pANCA is found only very rarely in healthy adults and children, healthy relatives of UC patients have an increased frequency of pANCA, indicating that pANCA may be an immunogenetic susceptibility marker.

Serum antibodies to cytoplasmic components of a neutrophil (ANCA) can be detected, for example, using indirect immunofluorescence microscopy of alcohol-fixed neutrophils. ANCA activity has been divided into two broad categories: cytoplasmic neutrophil staining (cANCA) and perinuclear to nuclear staining or cytoplasmic staining with perinuclear highlighting (pANCA). The term "anti-neutrophil cytoplasmic antibody" is synonymous with "ANCA" and encompasses both pANCA and cANCA. As used herein, the term "perinuclear anti-neutrophil cytoplasmic antibody" is synonymous with "pANCA" and refers to an antibody that reacts specifically with a neutrophil to give perinuclear to nuclear staining or cytoplasmic staining with perinuclear highlighting. The term pANCA-positive, when used in reference to a patient, means a patient having pANCA. The term "pANCA staining pattern" means the perinuclear to nuclear staining pattern or cytoplasmic staining pattern with perinuclear highlighting that distinguishes pANCA from cANCA.

As disclosed herein, a significant elevation in pANCA titer following colectomy and IPAA for UC indicates an increased risk of pouchitis development. As described in Example II, an enzyme-linked immunosorbent assay (ELISA) was used to determine pANCA titers preoperatively and at three month intervals following colectomy and IPAA. A single preoperative pANCA titer was not predictive of the development of pouchitis. However, when serial pANCA titers were compared, six of twelve patients (50%) who had a significantly elevated pANCA titer, as compared to an earlier pANCA titer, developed pouchitis within twelve months. In contrast, none of the patients lacking a significantly elevated pANCA titer following IPAA developed pouchitis within twelve months (see Table 1). Thus, the present invention provides a method of determining a risk of pouchitis development following a surgical procedure whereby colon is removed and an internal pouch is created on the basis of a pANCA titer that is significantly elevated as compared to an earlier pANCA titer.

The term "significantly elevated," as used herein in reference to a second pANCA titer or a subsequent pANCA titer, means a pANCA titer that is at least about two-fold greater than an earlier pANCA titer from the same patient. The term "comparable or reduced," as used herein in reference to a second pANCA titer or a subsequent pANCA titer, means a pANCA titer that is less than two-fold greater than an earlier pANCA titer.

The term "earlier pANCA titer," as used herein in reference to a subsequent pANCA titer, means the pANCA titer of a sample obtained from a patient prior to the time at which a sample was obtained for determination of the subsequent pANCA titer. For determining a first pANCA titer prior to the surgical procedure whereby a colon is removed and an internal pouch is created in a patient with UC, a sample is obtained from the patient prior to surgery, preferably not more than several months before surgery. For determining a first pANCA titer following the surgical procedure, a sample is obtained from the patient following surgery, preferably one to two months following surgery. For determining a second or subsequent pANCA titer, a sample is obtained at a later time, preferably at least one month later than the previous sample was obtained.

The term "increased risk," as used herein in reference to pouchitis development indicated by a significantly elevated second pANCA titer, refers to a probability of pouchitis development that is significantly higher than the probability of pouchitis development for a patient lacking a significantly elevated second pANCA titer. Similarly, the term increased risk, as used herein in reference to pouchitis development indicated by a significantly elevated subsequent pANCA titer, refers to a probability of pouchitis development that is significantly higher than the probability of pouchitis development for a patient lacking a significantly elevated subsequent pANCA titer.

The term "decreased risk," as used herein in reference to pouchitis development indicated by a comparable or reduced second pANCA titer, refers to a probability of pouchitis development that is significantly lower than the probability of pouchitis development for a patient lacking a comparable or reduced second pANCA titer. Similarly, the term decreased risk, as used herein in reference to pouchitis development indicated by a comparable or reduced subsequent pANCA titer, refers to a probability of pouchitis development that is significantly lower than the probability of pouchitis development for a patient lacking a comparable or reduced subsequent pANCA titer.

Anti-neutrophil cytoplasmic antibodies that produce a perinuclear staining pattern are present in 68–80% of UC patients and have been used previously to characterize clinically distinct subsets of UC patients. For example, the presence of pANCA has been associated with treatment-resistant left-sided ulcerative colitis; aggressive UC (Vecchi et al., *Digestion* 55:34–39 (1994)); and the requirement for surgery early in the course of UC (Boerr et al., *Gastroenterol*, 108:A785 (1995)).

An association also has been observed between the presence of pANCA and pouchitis following ileal pouch-anal anastomosis for UC (Sandborn et al., *Gastroenterol*, 104:A774 (1993); Patel et al., supra, 1994; Vecchi et al., *Lancet* 344:886–887 (1994); Sandborn et al., supra, 1995). In particular, the presence of pANCA is more frequent in those suffering from chronic pouchitis after IPAA for UC than in patients without pouchitis (see, for example, Sandborn et al., supra, 1995). In contrast to previous associations, the present invention is directed to the discovery that, when serial pANCA titers are determined prior to symptoms of disease, a significantly elevated pANCA titer as compared to an earlier pANCA titer indicates an increased risk of pouchitis development. Thus, the present invention provides that an increase in pANCA titer is useful as a diagnostic indicator of the risk of pouchitis development before symptoms of pouchitis are present.

Furthermore, previous observations relating pANCA and pouchitis have correlated the presence or absence of pANCA with disease. In contrast, as disclosed herein, an elevation in pANCA titer, rather than the presence of pANCA per se, is predictive of pouchitis development in UC patients following pouch surgery. Neither pANCA titer nor an elevation in pANCA titer previously has been associated with an increased risk of pouchitis development.

As used herein, the term "pANCA titer" means the reciprocal of the greatest dilution of a sample that is positive for pANCA under defined conditions. For example, the defined conditions can be a fixed neutrophil ELISA assay, where a dilution of a test sample that is at least two standard deviations above the same dilution of a negative control sample is defined as positive. For purposes of determining a pANCA titer, a negative control sample is a sample that does not contain pANCA. A convenient negative control sample can be a pANCA-negative sample from a healthy individual.

A variety of methods that are well known in the art can be used to determine if a diluted sample is positive for pANCA (see, for example, Saxon et al., *J. Allergy Clin. Immunol.* 86:202–209 (1990); Harlow and Lane, Antibodies: *A Laboratory Manual* New York: Cold Spring Harbor Laboratory (1988), each of which are incorporated herein by reference). However, titers that are to be compared, such as a first pANCA titer, second pANCA titer and one or more subsequent pANCA titers, for example, should be determined under the same defined conditions. Such conditions include the same amount and type of antigen used to determine if a diluted sample is positive for pANCA; the detection system used including, for example, the same enzyme if an enzyme-linked system is used or the same fluorochrome if a fluorescent detection system is used; and the same negative control sample.

A pANCA titer generally is determined using serial dilutions, such as two-fold serial dilutions or three-fold serial dilutions, in order to determine the greatest dilution that is positive for pANCA. A pANCA titer can be determined readily using two-fold serial dilutions of a serum sample, for example, and the ELISA assay described in Example IA. Serial dilutions such as 1:20, 1:40, 1:80, 1:160, 1:320, 1:640 and 1:1280 dilutions can be tested using, for example, a fixed neutrophil assay with an alkaline phosphatase detection system to determine if a diluted sample is positive for pANCA. In the presence of a chromogenic substrate such as p-nitrophenol phosphate, color development (measured by absorbance at 405 nm) can be used to determine if a diluted test sample is positive for pANCA by determining, for example, if the absorbance at 405 nm of the diluted test sample is at least two standard deviations above the absorbance at 405 nm of the same dilution of a negative control sample.

A particularly useful method for determining if a diluted sample is positive for pANCA is an immunoassay, in which an antibody specific for ANCA is used to detect ANCA in patient sera. The use of an enzyme-linked immunosorbent assay (ELISA); radioimmunoassay (RIA); or immunoassay based on fluorescent or chemiluminescent detection, for example, is encompassed within the invention.

A detectable secondary antibody is particularly useful in the methods of the invention. A useful secondary antibody is an antibody or combination of antibodies that bind pANCA specifically. Such a secondary antibody can be an anti-pANCA antibody that binds any epitope of pANCA. A particularly useful secondary antibody is an anti-IgG antibody having specificity for the class determining portion of pANCA. A useful secondary antibody is specific for the species of the pANCA to be detected. For example, if human serum is the sample to be assayed, mouse anti-human IgG can be a useful secondary antibody. A combination of different secondary antibodies also can be useful, provided that at least one antibody of the combination binds pANCA of UC.

A secondary antibody useful in an immunoassay of the invention can be obtained commercially or by techniques well known in the art. Such an antibody can be a polyclonal or, preferably, monoclonal antibody that binds ANCA specifically. For example, IgG reactive polyclonal antibodies can be prepared using IgG or Fc fragments of IgG as an immunogen to stimulate the production of antibodies in the antisera of an animal such as a rabbit, goat, sheep or rodent, for example (Harlow and Lane, supra, 1988).

A monoclonal antibody usefull in the practice of the invention can be obtained from a number of commercially available sources. In addition, an immunogen useful to generate a monoclonal antibody that binds ANCA selectively can be, for example, human IgG or a Fc fragment of human IgG, ANCA or a Fab fragment of ANCA. A hybridoma that produces a monoclonal selective for ANCA can be identified by screening hybridoma supernatants for the presence of antibodies that bind ANCA specifically (Harlow, supra, 1988). For example, such a screening method can be a radioimmunoassay or enzyme-linked immunosorbent assay using neutrophil and pANCA-positive sera.

A secondary antibody can be labeled, for example, with an enzyme, fluorochrome, chemiluminescent marker or radioisotope. In addition, a secondary antibody can be rendered detectable using a biotin-avidin linkage such that a detectable marker is associated with the secondary antibody. Labeling of the secondary antibody, however, should not impair binding of the secondary antibody to pANCA. If desired, a multiple antibody system can be used as the secondary antibody. In such a system, at least one of the antibodies is capable of binding pANCA of UC, and at least one of the antibodies can be readily detected or measured by analytical methods.

A secondary antibody can be rendered detectable by labeling with an enzyme such as horseradish peroxidase (HRP), alkaline phosphatase (AP), β-galactosidase or urease, for example. A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). A secondary antibody can be linked to an enzyme by methods well known in the art (Harlow and Lane, supra, 1988) or can be obtained from a number of commercial sources. For example, goat F(ab')2 anti-human IgG-alkaline phosphatase is a useful detectable secondary antibody that can be purchased from Jackson Immuno-Research (West Grove, Pa.).

A secondary antibody also can be rendered detectable by labeling with a fluorochrome. Such a fluorochrome emits light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine, for example, are fluorochromes that can be linked to a secondary antibody and used to determine the greatest dilution of a sample that is positive for pANCA. A particularly useful fluorochrome is fluorescein or rhodamine. Methods of conjugating and using these and other suitable fluorochromes are described, for example, in Van Vunakis and Langone, *Methods in Enzymoloy,* Volume 74, Part C (1991), which is incorporated herein by reference. A secondary antibody linked to a fluorochrome also can be obtained from commercial sources. For example, goat F(ab')2 anti-human IgG-FITC is available from Tago Immunologicals (Burlingame, Calif.).

A pANCA titer also can be determined using a secondary antibody labeled with a chemiluminescent marker. Such a chemiluminescent secondary antibody is convenient for sensitive, non-radioactive detection of pANCA and can be obtained commercially from various sources such as Amersham Lifesciences, Inc. (Arlington Heights, Ill.).

A secondary antibody further can be rendered detectable by labeling with a radioisotope. An iodine-125 labeled secondary antibody is a particularly useful detectable secondary antibody (see, for example, Harlow and Lane, supra, 1988).

A signal from a detectable secondary antibody can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of ANCA can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Methods of assaying for the presence or absence of a pANCA staining pattern also are well known in the art. Methods of cell staining using, for example, neutrophil, are useful for determining the subcellular localization of ANCA reactivity, thereby differentiating pANCA from cANCA. Immunocytochemistry or immunofluorescence is particularly useful for determining a pANCA staining pattern (see Example IB). A detectable secondary antibody that binds ANCA specifically, such as those described above, can be useful in such methods. For example, indirect immunofluorescence readily can be performed by incubating methanol-fixed neutrophil with a 1:20 dilution of human sera and detecting the complex formed with fluorescein-labeled F(ab')2 γ chain secondary antibody. The presence or absence of the pANCA staining pattern in the stained cells can be visualized using fluorescence microscopy as described in Saxon et al., supra, 1990, or in Example IA.

A pANCA titer can be determined using a sample obtained from any biological fluid such as whole blood, plasma or other bodily fluid or tissue having pANCA, preferably serum. Each of the multiple samples to be used in determining serial pANCA titers from the same patient are preferably the same type of biological fluid or tissue. As used herein, the term "patient" means any animal capable of producing pANCA including, for example, a human, non-human primate, rabbit, rat or mouse. A sample for the determination of a pANCA titer can be obtained from any such patient.

The methods of the invention for determining the risk of pouchitis development are useful in the post-operative medical management of patients that have had pouchitis surgery. A patient determined to have an increased risk of pouchitis development according to the methods of the invention can be treated prophylactically with any one of a number of therapies. Medical treatment for pouchitis includes antibiotics such as metronidazole, ciprofloxacin, amoxicillin or clavulanic acid, erythromycin and tetracycline; anti-inflammatory drugs such as mesalamine enemas, sulfasalazine and oral mesalamine; immunosuppressive drugs such as steroid enemas, oral steroids, azathioprine and cyclosporine enemas; nutritional agents such as short-chain fatty acid enemas or suppositories and glutamine suppositories; and inhibitors of oxygen radicals such as allopurinol (see, for example, Sandborn, *Gastroenterol,* 107:1856–1860 (1994); Hanauer, *New Engl. J. Med.* 334(13):841–848 (1996), each of which is incorporated herein by reference).

The methods of the invention are particularly useful for allowing the selective treatment of patients at increased risk for developing pouchitis and permitting low-risk patients to avoid the side-effects of unnecessary therapy. For example, side-effects associated with antibiotic treatment, which is a preferred course of therapy for pouchitis, make it undesirable to place low-risk patients on these drugs unnecessarily. The methods of the invention, which allow treatment of a patient with an increased risk of developing pouchitis before clinical symptoms are detectable, also can prevent development of the chronic form of pouchitis through early intervention. Accordingly, the methods of the invention for determining the risk of developing pouchitis can be useful in the earlier and more selective treatment of ulcerative colitis patients that have had pouch surgery.

The following examples are intended to illustrate but not limit the present invention.

EXAMPLE I

Techniques for detecting ANCA and pANCA

This example provides techniques for detecting ANCA and for determining a pANCA staining pattern.

A. Fixed neutrophil ELISA for detection of ANCA

A fixed neutrophil enzyme-linked immunosorbent assay was used to detect ANCA as described in Saxon et al., supra, 1990. Microtiter plates were coated with $2.5 \times 10^5$ neutrophils per well and treated with 100% methanol to fix the cells. Cells were incubated with 0.25% bovine serum albumin (BSA) in phosphate-buffered saline to block nonspecific antibody binding. Next, control and coded sera were added at a 1:100 dilution to the bovine serum/phosphate-buffered saline blocking buffer. Alkaline phosphatase conjugated goat F(ab')$_2$ anti-human immunoglobulin G (γ-chain specific) antibody (Jackson Immunoresearch Labs, Inc., West Grove, Pa.) was added at a 1:1000 dilution to label neutrophil bound antibody. A p-nitrophenol phosphate substrate solution was added and color development was allowed to proceed until absorbance at 405 nm in the positive control wells was 0.8–1.0 optical density units greater than the absorbance in blank wells. The results were expressed as percent of standard binding with pANCA-positive defined as an absorbance at 405 nm that is greater than two standard deviations (SD) above mean of control.

B. Indirect immunofluorescence assay for determination of a pANCA staining pattern Indirect immunofluorescent staining was performed on samples that were ANCA-positive by ELISA to determine whether the predominant staining pattern was perinuclear (pANCA) or cytoplasmic (cANCA). Glass slides containing approximately 100,000 neutrophils per slide were prepared by cytocentrifugation (Shandon Cytospin, Cheshire, England) and fixed in 100% methanol, air-dried, and stored at −20° C. The fixed neutrophils were incubated with human sera diluted (1:20), and the reaction was visualized with fluorescein-labeled F(ab')$_2$ γ chain-specific antibody as described in Saxon et al., supra, 1990. The slides were examined using an epifluorescence-equipped Olympus BH-2 microscope (Olympus, Lake Success, N.Y.).

EXAMPLE II

Determination of the risk of early pouchitis development following IPAA

This example demonstrates that the risk of the development of early-onset pouchitis following pouch surgery varies according to whether there is a post-operative elevation in pANCA titer.

A. Determination of pANCA titer pANCA titers were measured prospectively in UC patients before and after ileal pouch anal anastomosis. Serum was drawn before IPAA and at three month intervals after surgery; serial dilutions of serum samples were analyzed for ANCA by fixed neutrophil ELISA as described in Example IA. The pANCA titer was determined as the reciprocal of the highest dilution that was positive for pANCA, and pANCA-positive was defined as greater than two standard deviations (SD) above mean of control. The control sera for use in these experiments was pANCA-negative sera from healthy individuals. Positive results were confirmed by a perinuclear staining pattern using indirect immunofluorescence as described in Example IB.

B. Data correlating increase in pANCA titer following IPAA for UC with the development of early-onset pouchitis All twenty-one study patients were ANCA-positive and nineteen patients had ANCA with perinuclear staining (pANCA-positive). Six of the pANCA-positive patients (32%) developed early-onset pouchitis. Early-onset pouchitis was diagnosed in patients meeting both clinical and endoscopic criteria within twelve months of IPAA. An insignificant correlation was noted between preoperative pANCA titer and the development of early-onset pouchitis: pouchitis developed in 40% of pANCA-positive patients with a preoperative titer greater than 800 and in 29% of pANCA-positive patients with a preoperative titer less than or equal to 800. The difference in the frequency of pouchitis development between the two groups was not significant.

In the postoperative period, fourteen patients (74%) remained pANCA-positive, two patients (11%) became ANCA-negative, and three patients (16%) became ANCA-negative but later reconverted to pANCA-positive. Following ileal pouch anal anastomosis, pANCA titers decreased and remained low in six patients (32%); increased and then decreased in one patient (5%); increased and remained high in five patients (26%); and decreased and then increased in seven patients (37%) as summarized in Table 1. Of the 12 patients (50%) who had a significantly elevated pANCA titer following IPAA, six developed early pouchitis as compared to none of the seven patients whose pANCA levels did not increase after IPAA. In three of the six patients who developed early pouchitis, the elevation in pANCA titer occurred before the clinical diagnosis. In the remaining three patients, an elevated pANCA titer was noted on the first pANCA assay following the diagnosis of pouchitis.

TABLE 1

| Pre-operative to post-operative change in pANCA titer | Change in subsequent post-operative pANCA titers | Percentage of patients | Number of Patients | Number of patients with early-onset pouchitis |
|---|---|---|---|---|
| decrease | no change | 32% | 6 | 0 of 7 |
| increase | decrease | 5% | 1 | |
| increase | no change | 26% | 5 | 6 of 12 |
| decrease | increase | 37% | 7 | |

Although the invention has been described with reference to the examples above, it should be understood that various modifications can be made without departing from the spirit of the invention. Accordingly, the invention is limited only by the following claims.

We claim:

1. A method of determining a risk of pouchitis development following a surgical procedure whereby colon is removed and an internal pouch is created in a patient with ulcerative colitis (UC), comprising:
   a) determining a first perinuclear anti-neutrophil cytoplasmic antibody (pANCA) titer, wherein said first pANCA titer is determined following said surgical procedure;
   b) determining a second pANCA titer at a later time; and
   c) comparing said first pANCA titer and said second pANCA titer, wherein a significantly elevated second pANCA titer indicates an increased risk of pouchitis development.

2. The method of claim 1, wherein steps a) and b) further comprise assaying for the presence or absence of a pANCA staining pattern.

3. The method of claim 1, wherein said first and second pANCA titers are determined using an immunoassay.

4. The method of claim 3, wherein said immunoassay is a fixed neutrophil enzyme-linked immunosorbent assay.

5. The method of claim 1, further comprising:
   d) determining one or more subsequent pANCA titers at one or more subsequent times; and
   e) comparing a subsequent pANCA titer with an earlier pANCA titer, wherein a significantly elevated subsequent pANCA titer indicates an increased risk of pouchitis development.

6. The method of claim 5, wherein steps a), b) and d) further comprise assaying for the presence or absence of a pANCA staining pattern.

7. The method of claim 5, wherein said first pANCA titer, second pANCA titer and one or more subsequent pANCA titers are determined using an immunoassay.

8. The method of claim 7, wherein said immunoassay is a fixed neutrophil enzyme-linked immunosorbent assay.

9. The method of claim 1, wherein said pouchitis is early-onset pouchitis.

10. The method of claim 1, wherein said pouchitis is acute pouchitis.

11. The method of claim 1, wherein said pouchitis is chronic pouchitis.

12. The method of claim 1, wherein said surgical procedure is colectomy with ileal pouch anal anastomosis.

13. A method of determining a risk of pouchitis development following a surgical procedure whereby colon is removed and an internal pouch is created in a patient with ulcerative colitis (UC), comprising:

a) determining a first perinuclear anti-neutrophil cytoplasmic antibody (pANCA) titer, wherein said first pANCA titer is determined prior to said surgical procedure;

b) determining a second pANCA titer following said surgical procedure; and c) comparing said first pANCA titer and said second pANCA titer, wherein a significantly elevated second pANCA titer indicates an increased risk of pouchitis development.

14. The method of claim 13, wherein steps a) and b) further comprise assaying for the presence or absence of a pANCA staining pattern.

15. The method of claim 13, wherein said first and second pANCA titers are determined using an immunoassay.

16. The method of claim 15, wherein said immunoassay is a fixed neutrophil enzyme-linked immunosorbent assay.

17. The method of claim 13, further comprising:

d) determining one or more subsequent pANCA titers at one or more subsequent times; and e) comparing a subsequent pANCA titer with an earlier pANCA titer, wherein a significantly elevated subsequent pANCA titer indicates an increased risk of pouchitis development.

18. The method of claim 17, wherein steps a), b) and d) further comprise assaying for the presence or absence of a pANCA staining pattern.

19. The method of claim 17, wherein said first pANCA titer, second pANCA titer and one or more subsequent pANCA titers are determined using an immunoassay.

20. The method of claim 19, wherein said immunoassay is a fixed neutrophil enzyme-linked immunosorbent assay.

21. The method of claim 13, wherein said pouchitis is early-onset pouchitis.

22. The method of claim 13, wherein said pouchitis is acute pouchitis.

23. The method of claim 13, wherein said pouchitis is chronic pouchitis.

24. The method of claim 13, wherein said surgical procedure is colectomy with ileal pouch anal anastomosis.

25. A method of determining the risk of pouchitis development following a surgical procedure whereby colon is removed and an internal pouch is created in a patient with ulcerative colitis (UC), comprising:

a) determining a first perinuclear anti-neutrophil cytoplasmic antibody (pANCA) titer, wherein said first pANCA titer is determined following said surgical procedure;

b) determining a second pANCA titer at a later time; and c) comparing said first pANCA titer and said second pANCA titer, wherein a comparable or reduced second pANCA titer indicates a decreased risk of pouchitis development.

26. The method of claim 25, further comprising:

d) determining one or more subsequent pANCA titers at one or more subsequent times; and e) comparing a subsequent pANCA titer with an earlier pANCA titer, wherein a comparable or reduced subsequent pANCA titer indicates a decreased risk of pouchitis development.

* * * * *